(12) United States Patent
Bargon et al.

(10) Patent No.: US 10,779,844 B2
(45) Date of Patent: Sep. 22, 2020

(54) SURGICAL TISSUE FUSION INSTRUMENT

(71) Applicant: Aesculap AG, Tuttlingen (DE)

(72) Inventors: Rainer Bargon, Tuttlingen (DE); Bernd Blender, Mühlheim a.d. Donau (DE); Stefan Eick, Tuttlingen (DE); Nikolaus Hafner, Tuttlingen (DE); Patrick Heizmann, Hüfingen (DE); Eugen Herner, Villingen-Schwenningen (DE); Christian Huber, Mühlheim (DE); Christof Merckle, Mannheim (DE); Erich Odermatt, Schaffhausen (CH); Christoph Rothweiler, Donaueschingen (DE)

(73) Assignee: AESCULAP AG, Tuttlingen (DE)

(*) Notice: Subject to any disclaimer, the term of this patent is extended or adjusted under 35 U.S.C. 154(b) by 209 days.

(21) Appl. No.: 15/505,348

(22) PCT Filed: Mar. 18, 2016

(86) PCT No.: PCT/EP2016/055981
§ 371 (c)(1),
(2) Date: Feb. 21, 2017

(87) PCT Pub. No.: WO2016/150857
PCT Pub. Date: Sep. 29, 2016

(65) Prior Publication Data
US 2019/0150964 A1    May 23, 2019

(30) Foreign Application Priority Data

Mar. 20, 2015 (DE) .......... 10 2015 205 057

(51) Int. Cl.
*A61B 18/14* (2006.01)
*A61B 17/285* (2006.01)
(Continued)

(52) U.S. Cl.
CPC ............ *A61B 17/285* (2013.01); *A61B 17/11* (2013.01); *A61B 17/2833* (2013.01);
(Continued)

(58) Field of Classification Search
CPC ................... A61B 18/1442; A61B 18/1445
See application file for complete search history.

(56) References Cited

U.S. PATENT DOCUMENTS

2003/0216733 A1* 11/2003 McClurken ............ A61B 18/14
606/51
2005/0184121 A1 8/2005 Heinrich
(Continued)

FOREIGN PATENT DOCUMENTS

EP        0722696        7/1996

*Primary Examiner* — Michael F Peffley
*Assistant Examiner* — Bo Ouyang
(74) *Attorney, Agent, or Firm* — Lewis Kohn & Walker LLP; David M. Kohn

(57) ABSTRACT

Surgical tissue fusion instrument having two gripping structures which are movable relative to each other, are designed for gripping and bringing together biological tissue sections, and are assigned heat-generating means designed in such a way that tissue fusion takes place between the biological tissue sections by heat being supplied in the area of the gripping structures. At least one gripping structure is assigned a fluid-conducting system, which is designed to supply at least one liquid or flowable additive to the tissue sections during a tissue fusion process.

13 Claims, 7 Drawing Sheets

Figure 1:
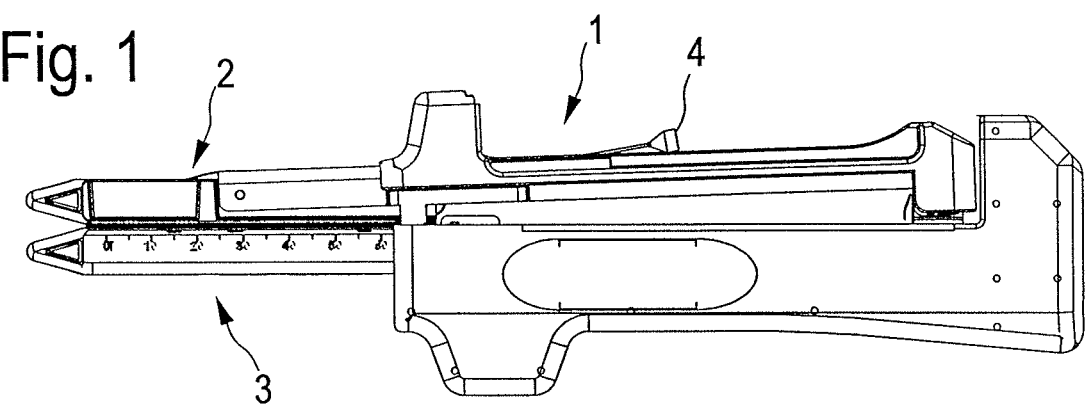

(51) Int. Cl.
*A61B 17/11* (2006.01)
*A61B 17/28* (2006.01)
*A61B 18/00* (2006.01)
*A61B 17/00* (2006.01)
*A61B 17/115* (2006.01)
*A61B 17/072* (2006.01)
*A61B 17/29* (2006.01)

(52) U.S. Cl.
CPC ...... *A61B 17/2841* (2013.01); *A61B 18/1442* (2013.01); *A61B 18/1445* (2013.01); *A61B 17/00491* (2013.01); *A61B 17/072* (2013.01); *A61B 17/1155* (2013.01); *A61B 2017/00504* (2013.01); *A61B 2017/00884* (2013.01); *A61B 2017/00889* (2013.01); *A61B 2017/00893* (2013.01); *A61B 2017/1125* (2013.01); *A61B 2017/2808* (2013.01); *A61B 2017/2948* (2013.01); *A61B 2018/0063* (2013.01); *A61B 2018/00166* (2013.01); *A61B 2018/00196* (2013.01); *A61B 2018/00404* (2013.01); *A61B 2018/00601* (2013.01); *A61B 2018/00619* (2013.01); *A61B 2018/00744* (2013.01); *A61B 2018/145* (2013.01); *A61B 2018/1412* (2013.01); *A61B 2018/1455* (2013.01); *A61B 2218/002* (2013.01)

(56) References Cited

U.S. PATENT DOCUMENTS

| | | |
|---|---|---|
| 2010/0069903 A1 | 3/2010 | Allen, IV et al. |
| 2010/0116428 A1 | 5/2010 | Trascinelli et al. |
| 2010/0243706 A1* | 9/2010 | Cohen .............. A61B 17/07207 227/176.1 |
| 2011/0098700 A1 | 4/2011 | Tamai et al. |
| 2011/0278246 A1 | 11/2011 | Daily |
| 2013/0006227 A1* | 1/2013 | Takashino .......... A61B 18/1445 606/13 |
| 2013/0090645 A1 | 4/2013 | Weisshaupt et al. |
| 2014/0005668 A1 | 1/2014 | Rhee et al. |

* cited by examiner

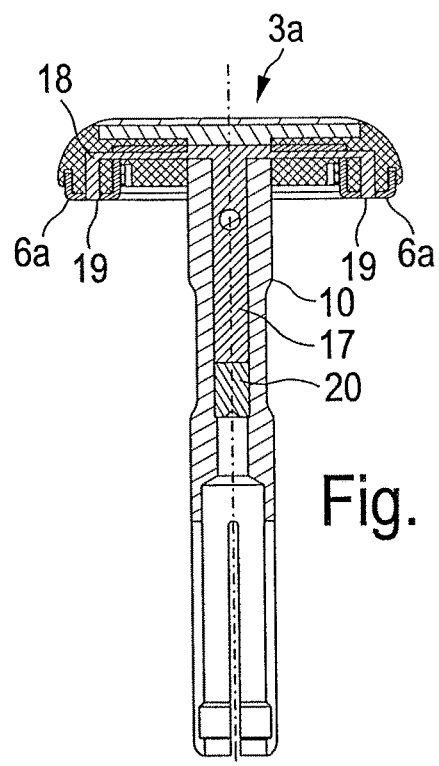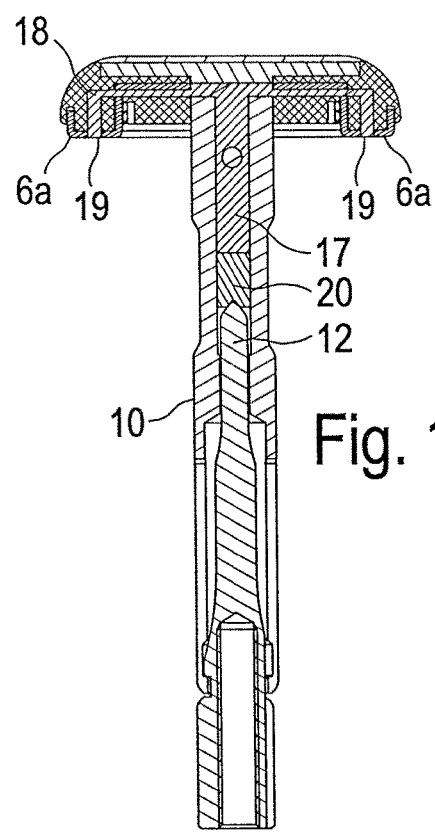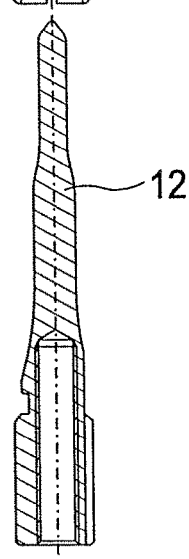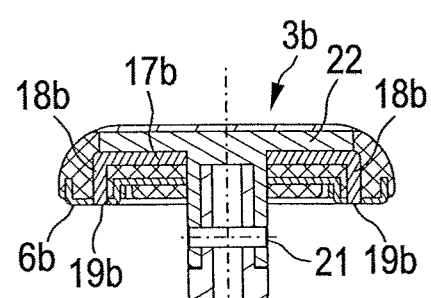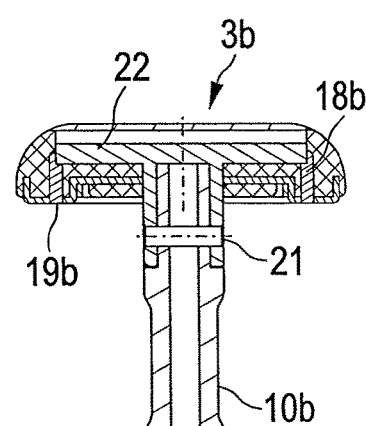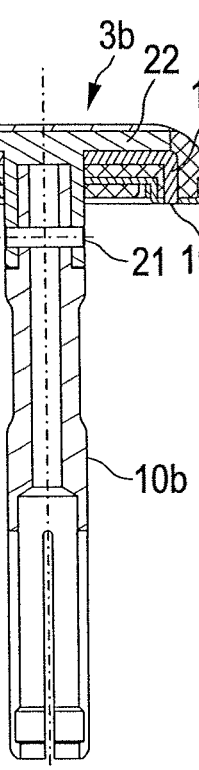
Fig. 10
Fig. 11
Fig. 12
Fig. 13

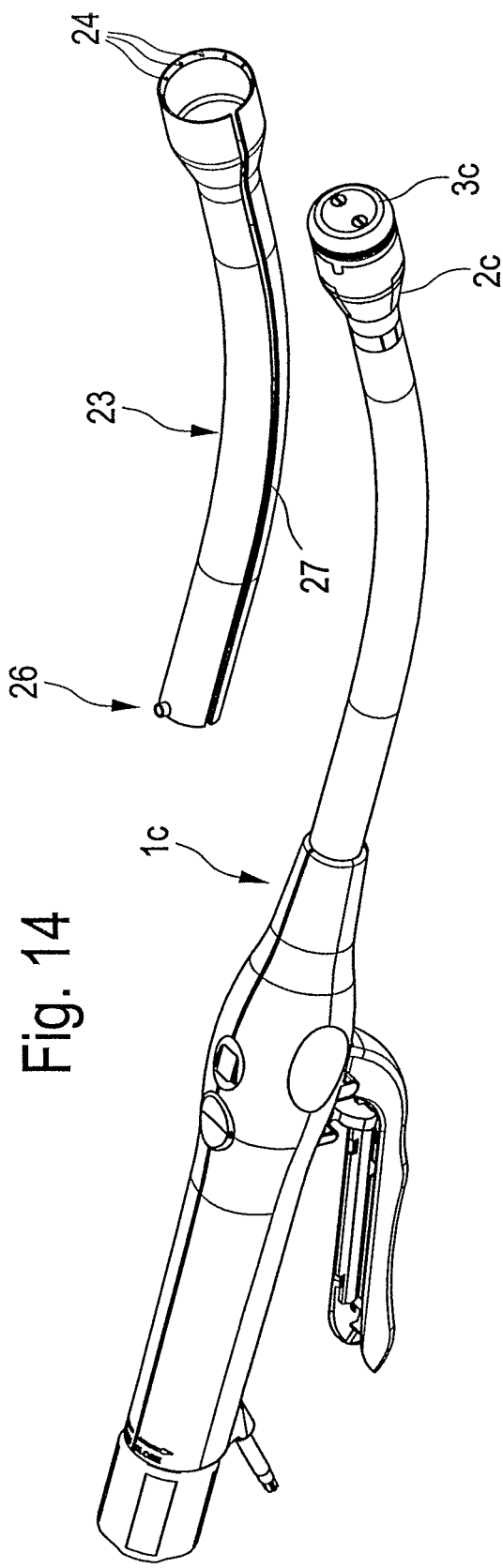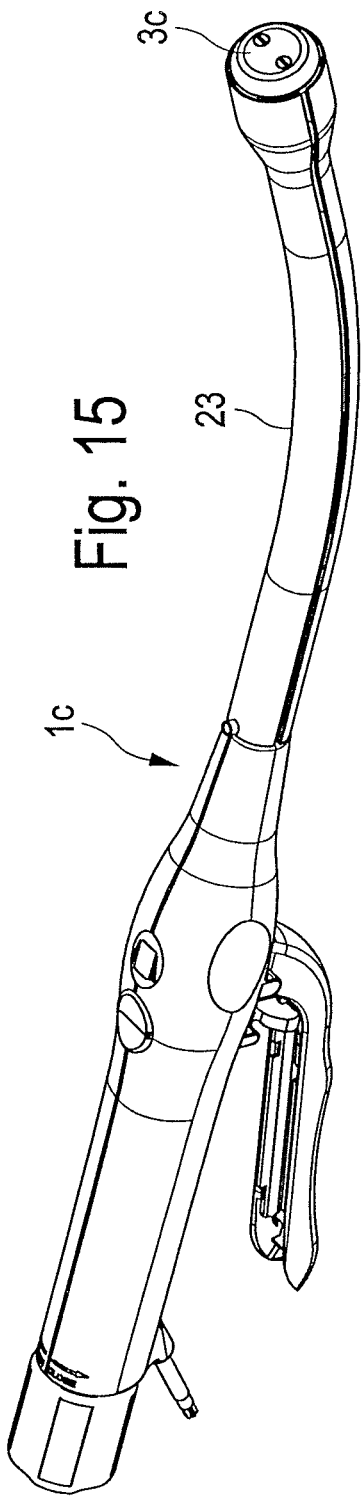

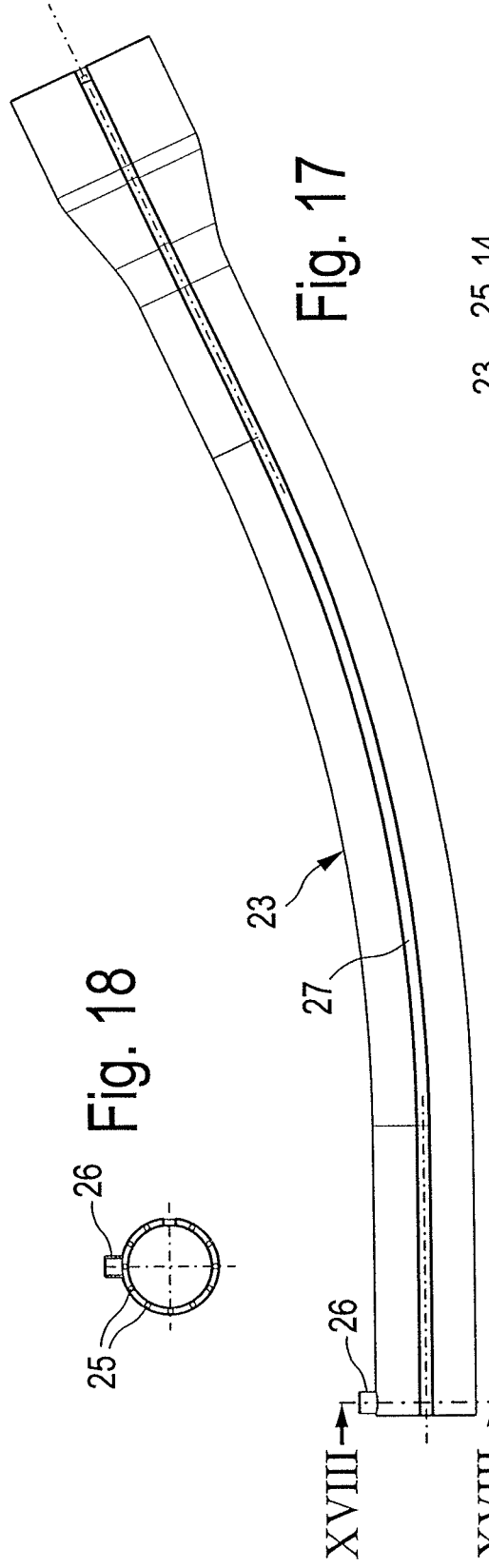
Fig. 17
Fig. 18
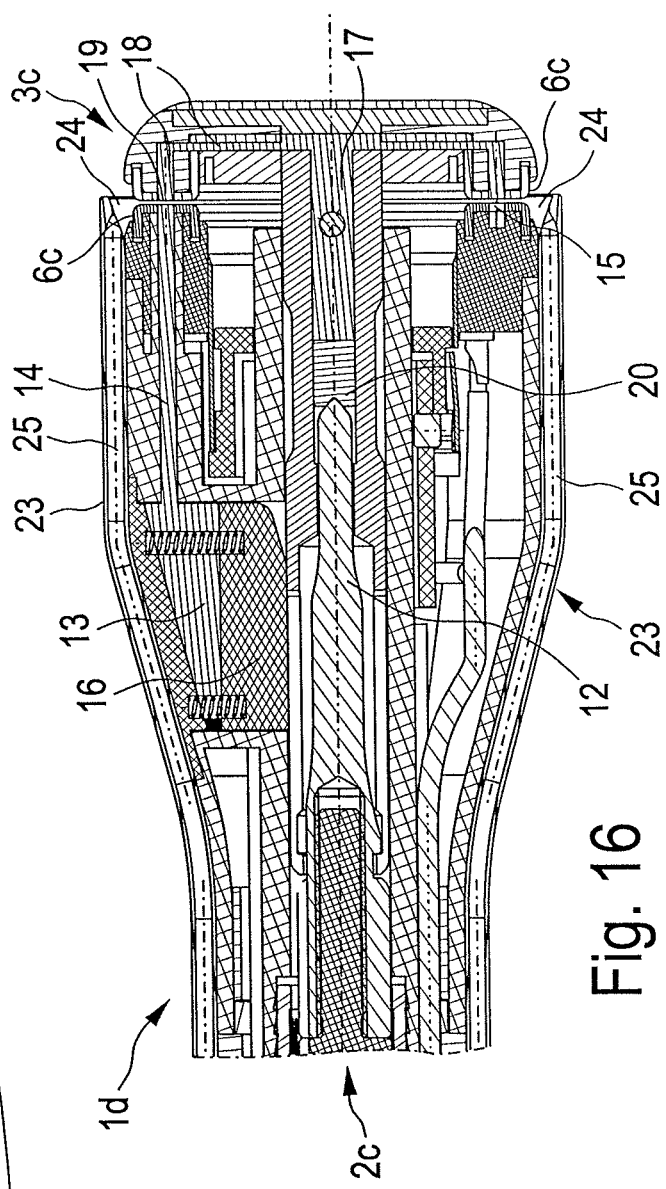
Fig. 16

SURGICAL TISSUE FUSION INSTRUMENT

This application is a United States National Stage Application claiming the benefit of priority under 35 U.S.C. 371 from International Patent Application No. PCT/EP2016/055981 filed Mar. 18, 2016, which claims the benefit of priority from German Patent Application Serial No. DE 102015205057.2 filed Mar. 20, 2015, the entire contents of which are herein incorporated by reference.

The invention relates to a surgical tissue fusion instrument with two gripping structures which are movable relative to each other, are designed for gripping and bringing together biological tissue sections, and are assigned heat-generating means designed in such a way that tissue fusion takes place between the biological tissue sections by heat being supplied in the area of the gripping structures.

Tissue fusion instruments of this kind are provided as linear instruments or as circular instruments. A linear surgical tissue fusion instrument has two forceps-like gripping structures which are movable toward each other, in order to grip corresponding biological tissue sections between them and connect to each other. Circular surgical tissue fusion instruments have a base part, with an anvil part that is movable coaxially with respect to the base part. The clamping and connecting take place between the anvil part and the base part, wherein the anvil part is mounted displaceably in the base part via an anvil shaft. The surgical tissue fusion instruments according to the invention create a connection between biological tissue sections, preferably without additional mechanical connecting means such as staples, sutures or the like. Accordingly, a surgical tissue fusion instrument of this kind is designed in particular without staples. According to the invention, however, provision is also made that, in addition to having the heat-generating means, a tissue fusion instrument also has devices for supplementary introduction of mechanical connection means such as, in particular, staples, in order to assist or strengthen the tissue fusion by a stapled suture or another mechanical connecting suture. Corresponding staples are preferably driven into the tissue sections in a simultaneous, previous or subsequent work step. A tissue fusion instrument according to the invention can have stapler function areas which alternate with or are parallel to corresponding functional surfaces of the heat-generating means, and which are assigned storage means or magazines for stocking the staples.

DE 10 2010 020 664 A1 discloses a surgical tissue fusion instrument having two gripping structures which are movable relative to each other and in which electrodes are integrated which, when current is applied, transmit high-frequency electromagnetic waves through the biological tissue sections that are to be connected and which cause heat to be introduced into these tissue sections. A desired tissue fusion thus takes place between the biological tissue sections. To aid and promote the connection between the biological tissue sections, a disk made of a medically acceptable material is provided which, when the gripping structures are brought together, is held sandwiched between the tissue sections that are to be connected. Moreover, the tissue fusion instrument has a cutting device which, after the tissue fusion has taken place, permits separation of the tissue sections that are fused to each other. This may be advantageous in particular in anastomosis of hollow organs, so as to be able to form a common channel through the hollow organs after fusion of the tissue sections.

The object of the invention is to make available a surgical tissue fusion instrument which is of the kind mentioned at the outset and which permits tissue fusion that is further improved in relation to the prior art.

This object is achieved by the fact that at least one gripping structure is assigned a fluid-conducting system, in particular with at least one gripping structure having a fluid-conducting system which is designed for the delivery of at least one liquid or flowable additive to the tissue sections during a tissue fusion procedure.

The liquid or flowable additive aids or promotes the fusion of the biological tissue sections. The corresponding additive can have one or more of the following functions: promoting wound healing, increasing the strength of the connection between the tissue sections, improving an electrical or thermal conductivity between the heat-generating means and the tissue sections, providing thermal or electrical insulation in areas outside the area of heat introduction, avoiding undesired adherence of the tissue sections to the gripping structures, reducing the thermal tissue damage outside the connection site, improving the tissue contact (in particular with respect to a sensor or a sensor arrangement of the tissue fusion instrument), providing improved introduction of energy or heat, providing improved visualization of the biological tissue sections that are to be fused to each other, and finally the resorbability of the additive.

The at least one additive is stored in a liquid form, in particular as a solution, suspension or emulsion, preferably as an aqueous solution, aqueous suspension or aqueous emulsion, or in a flowable form, i.e. in particular in the form of particles, a paste, a melt or gel, preferably a hydrogel, so as to be able to flow in, during the introduction of heat during a tissue fusion procedure in the area of the tissue sections that are to be connected, in particular under the effect of pressure and/or temperature.

The delivery of the at least one liquid or flowable additive can in particular be effected by pressure build-up or by capillary action. The delivery of the at least one additive is either effected necessarily by the initiation of the tissue fusion procedure or by means of a separate actuation mechanism as required.

The solution according to the invention is used both for circular and also for linear surgical tissue fusion instruments. The tissue fusion procedure comprises bringing the movable gripping structures together, thereby clamping the biological tissue sections between these gripping structures, and subsequently introducing heat by use of suitable heat-generating means.

The heat-generating means provided are in particular high-frequency or radio-frequency electrodes, which are integrated in the gripping structures. Alternatively, laser units, sonotrodes, microwave generators, plasma generators, resistance heaters such as cauters or a combination of two or more of said heat-generating means, or other heat-generating devices, can be provided as heat-generating means and integrated in the gripping structures. The essential aspect of all the heat-generating means that can be used according to the invention is that the tissue sections are heated, in a manner spatially limited to the critical connection sites, such that structural changes of the tissue sections lead to the tissue sections cohesively fusing with each other.

In one embodiment of the invention, the surgical tissue fusion instrument has a liquid or flowable additive which is preferably contained in the fluid-conducting system, in particular in at least one fluid-conducting channel and/or in at least one fluid reservoir of the fluid-conducting system.

In a further embodiment of the invention, the additive is chosen from the group comprising or consisting of salt, for example inorganic salt, wax, fat, fatty acid, alcohol, synthetic polymer, biopolymer (naturally occurring polymer), technical biopolymer (industrially produced biopolymer), protein, extracellular protein, serum protein, glycoprotein, polyamino acid, polyhomoamino acid, polyheteroamino acid, oligopeptide, amino acid, polysaccharide, mucopolysaccharide, oligosaccharide, monosaccharide, lipid, glycolipid, medicament, medical or pharmaceutical active substance, growth factor, cyanoacrylate and mixtures thereof.

The salt can be chosen from the group comprising or consisting of alkali metal halide, alkaline earth metal halide, phosphate, alkali metal phosphate, alkaline earth metal phosphate and mixtures thereof.

The salt can in particular be chosen from the group comprising or consisting of sodium chloride, potassium chloride, barium chloride, magnesium chloride, calcium chloride, sodium phosphate, potassium phosphate, barium phosphate, magnesium phosphate, calcium phosphate, mixed phosphates thereof and mixtures thereof.

The synthetic polymer can be chosen, for example, from the group comprising or consisting of polyglycolide, polylactide, polytrimethylene carbonate, poly-ε-caprolacton, poly-3-hydroxybutyrate, poly-4-hydroxybutyrate, poly-5-hydroxybutyrate, poly-6-hydroxybutyrate and mixtures thereof.

The protein can be chosen from the group comprising or consisting of collagen, gelatin, elastin, reticulin, laminin, fibronectin, fibrillin, albumin, derivatives thereof, peptide fragments thereof, subunits thereof and mixtures thereof.

The protein can in particular be collagen, which is chosen from the group comprising or consisting of type I collagen, type II collagen, type III collagen, type VI collagen, derivatives thereof, peptide fragments thereof, subunits thereof and mixtures thereof.

The polysaccharide can be chosen from the group comprising or consisting of starch, modified starch, amylose, amylopectin, dextran, hyaluronic acid, heparin, heparan sulfate, chondroitin-4-sulfate, chondroitin-6-sulfate, dermatan sulfate, keratan sulfate, derivatives thereof and mixtures thereof.

The medicament can be chosen from the group comprising or consisting of antibiotics, cytostatics, spasmolytics, platelet aggregation inhibitors, anticoagulants, hormones, gastrointestinal therapeutics, local anesthetics, antihypertensives, anti-inflammatories, analgesics and mixtures thereof.

The medical or pharmaceutical active substance can be chosen from the group comprising or consisting of antimicrobial, in particular antibiotic, active substance, hemostyptic active substance, anti-inflammatory active substance, active substance that promotes wound healing, analgesic active substance, growth-promoting active substance and mixtures thereof.

The antimicrobial active substance can be chosen from the group comprising or consisting of silver, silver salt, antibiotic, polyhexamethylene biguanide and mixtures thereof.

The growth factor can be chosen from the group comprising or consisting of fibroblast growth factor (FGF), transforming growth factor (TGF), platelet-derived growth factor (PDGF), epidermal growth factor (EGF), granulocyte-macrophage colony stimulating factor (GMCSF), vascular endothelial growth factor (VEGF), insulin-like growth factor (IGF), hepatocyte growth factor (HGF), interleukin, nerve growth factor (NGF), hematopoietic growth factor and mixtures thereof.

In a further embodiment of the invention, the additive is an additive that improves tissue contact. In particular, the additive can be an additive that is designed to improve the tissue contact to a sensor or to a sensor arrangement of the surgical tissue fusion instrument. An additive of this kind can in particular be an immersion medium, for example glycerol, hydrogels or oils with a defined refractive index.

In a further embodiment of the invention, the additive is an additive that is designed to improve an image-based evaluation of the biological tissue sections to be fused to each other or of biological tissue sections already fused to each other. A suitable additive can in particular be designed as contact material for better coupling-in of ultrasound, for example, to permit image-based evaluation. Suitable additives can be, for example, hydrogels of carbomers or derivatives thereof, plant lipogels (oleogels), synthetic lipogels (oleogels), mineral lipogels (oleogels), hyaluronic acid or biological gels such as aloe vera.

In a further embodiment of the invention, the additive is an additive that is designed to improve the input of energy or heat into the biological tissue sections to be fused to each other. A suitable additive is, for example, in the form of glycerol, biological oils, synthetic oils, mineral oils, hydrogels or lipogels (oleogels).

In a further embodiment of the invention, the additive is an energy-converting or energy-absorbing additive that is designed to bring about a positioned conversion from one energy form, for example light energy, to thermal energy. A suitable additive can be, for example, in the form of metallic or metallized particles such as silver particles, carbon particles or other absorbing materials or nanostructures. The additive can be applied in the form of particles, emulsions, melts or in a dissolved form.

In a further embodiment of the invention, the additive is an energy-coupling additive that is designed in particular to introduce inductive energy. Such an additive can, for example, be in the form of ferromagnetic particles, graphite or carbon-containing materials.

In a further embodiment of the invention, the additive is a tissue-structure-labelling additive that is designed for labelling the biological tissue sections to be fused to each other or biological tissue sections already fused to each other. A suitable additive can be, for example, a fluorescence dye. The use of fluorescence dyes has in particular the advantage that the structure of the tissue sections can be detected by means of an optical sensor arrangement contained in the surgical tissue fusion instrument.

In a further embodiment of the invention, the additive is a tissue-density-labelling additive that is designed for labelling the density of the biological tissue sections to be fused to each other or of biological tissue sections already fused to each other, for example by means of ultrasound. A suitable additive, for example, is in the form of gas-filled microbubbles.

In a further embodiment of the invention, the additive is an X-ray contrast medium, for example barium sulfate, or an iodine-containing contrast medium. A particular advantage of this is that it permits an image-based evaluation of the biological tissue sections to be fused to each other or of biological tissue sections already fused to each other.

In a further embodiment of the invention, the fluid-conducting system has at least one fluid-conducting channel, which is integrated in one of the two gripping structures. The integration of the at least one fluid-conducting channel in one of the two gripping structures permits simple delivery of a suitably liquid or flowable fluid, in the form of at least one additive, directly in the area of the connection site.

In a further embodiment of the invention, the fluid-conducting system has at least one fluid reservoir, which is connected to the fluid-conducting channel. The fluid reservoir can be integrated in the surgical tissue fusion instrument or can be arranged as a separate unit distinct from the tissue fusion instrument. When the fluid reservoir is designed separate from the tissue fusion instrument, an attachment system is advantageously provided in order to be able to connect the fluid reservoir to a corresponding fluid-conducting channel of the tissue fusion instrument.

In a further embodiment of the invention, at least one gripping structure is provided with fluid outlet openings, into which the at least one fluid-conducting line opens. The fluid outlet openings are preferably oriented on the gripping structure such that the liquid or flowable additive is delivered directly to the connection site of the biological tissue sections during a tissue fusion procedure.

In a further embodiment of the invention, the at least one fluid reservoir is integrated in at least one gripping structure. The liquid or flowable additive, which is stored in the fluid reservoir, therefore only has to travel a short distance in order to be delivered from the fluid reservoir and optionally the fluid-conducting channels through the fluid outlet openings to the fusion area of the tissue sections and therefore to the connection site between the tissue sections.

In a further embodiment of the invention, the fluid reservoir and/or the fluid-conducting channel has a storage volume that is variable depending on an actuation mechanism. The variable storage volume permits a pressure-dependent discharge of the liquid and flowable additive through the fluid outlet openings in the direction of the tissue sections that are to be connected.

In a further embodiment of the invention, the actuation mechanism is operatively connected to an actuation unit for bringing the gripping structures together. Accordingly, an actuation of the gripping structures in the direction of their closed position necessarily also leads to a fluid discharge of the additive in the area of the fluid outlet openings. An additional, separate actuation is not needed to permit discharge of the additive.

In a further embodiment of the invention, the fluid reservoir and/or the actuation mechanism are positioned separate from the tissue fusion instrument, and releasable attachment means are provided for producing or cancelling a connection between the fluid reservoir and/or the actuation mechanism and the at least one fluid-conducting channel of the tissue fusion instrument. The attachment means are preferably mechanical connection systems in the form of hose couplings, Luer lock or Luer slip connections or the like.

Advantageously, the fluid outlet openings in the at least one gripping structure are positioned in active areas of the heat-generating means. The fluid outlet openings are advantageously integrated in at least one electrode arrangement, which is assigned to the heat-generating means. The electrode arrangement is advantageously designed as a high-frequency electrode arrangement (HF electrode) or as a radio-frequency electrode arrangement.

In a further embodiment of the invention, the fluid outlet openings are provided in a movably mounted actuation wall of the at least one fluid-conducting channel or fluid reservoir, which actuation wall, depending on an activation of the actuation unit, is movable in order to bring together the gripping structures. The movement results in the desired pressure-dependent fluid discharge of the additive in the direction of the connection site of the tissue sections. The actuation wall is advantageously mounted in a floating manner in a structural body of the gripping structure. The actuation wall can in particular be formed by an electrode wall of the electrode arrangement.

The fluid outlet openings are preferably integrated in a linearly movable anvil part of a circular tissue fusion instrument, said anvil part serving as gripping structure. The anvil part advantageously comprises at least one fluid reservoir and at least one fluid-conducting channel. The actuation wall is advantageously integrated in the anvil part. It is thereby possible, in a simple manner, to achieve direct delivery of the at least one additive to the fusion area of the biological tissue sections between the gripping structures, i.e. between the anvil part and a base part of the circular tissue fusion instrument. The anvil part advantageously has an anvil head and an anvil shaft, which is mounted in a longitudinally displaceable manner in the base part. The base part advantageously has corresponding heat input means, preferably in the form of an electrode arrangement. The anvil head can additionally be provided with complementary heat-generating means, particularly in the form of an electrode arrangement coordinated with the electrode arrangement in the base part. Electrode arrangements cooperating with each other as heat-generating means are preferably provided in the anvil part and in the base part. Alternatively, either the anvil part or the base part can be provided with a heat-generating means.

An actuation wall of the fluid reservoir is advantageously designed as an actuation piston of the actuation mechanism, which actuation piston is moved in accordance with a movement of the anvil part relative to the base part. Accordingly, an actuation of the gripping structures of the circular tissue fusion instrument necessarily brings about a discharge of the additive from the fluid outlet openings to the connection site between the biological tissue sections.

In a further embodiment of the invention, the fluid-conducting system is integrated in a carrier housing which encloses at least a partial area of the tissue fusion instrument and which is provided with the at least one fluid-conducting channel or the fluid reservoir and also with the fluid outlet openings. The carrier housing can advantageously be produced separately from the tissue fusion instrument and, after being produced and then filled with the additive, can be connected to the tissue fusion instrument. The carrier housing is adapted to corresponding outer contours of the tissue fusion instrument, according to the linear or circular configuration of the tissue fusion instrument.

In a further embodiment of the invention, the fluid outlet openings in the carrier housing are positioned in the area of the dividing plane between the gripping structures, and the fluid outlet openings are directed radially from the outside toward the dividing plane. The positioning of the fluid outlet openings is in relation to the position of the carrier housing mounted on the tissue fusion instrument. The radial arrangement of the fluid outlet openings permits a fluid discharge of the additive from the outside toward the connection site of the tissue sections.

In a further embodiment of the invention, a circular tissue fusion instrument is provided, and the carrier housing is designed as a hollow profile body which forms a sleeve-shaped or tubular enclosure around a base part of the circular tissue fusion instrument and which is provided with an expansion slit extending along its entire length, so as to be able to mount the hollow profile body on the base part or detach it therefrom. The expansion slit allows the hollow profile body to be clipped onto or removed from the base part. The hollow profile body is preferably mounted on or removed from the base part without the use of tools. The hollow profile body comprises the fluid outlet openings which, in the assembled state, advantageously extend in the direction of the connection site between the gripping structures. In addition, the hollow profile body comprises at least one fluid-conducting channel. The hollow profile body can be provided with an attachment nozzle for the connection to a fluid reservoir. Alternatively, the hollow profile body itself can also comprise the fluid reservoir. Advantageously, the hollow profile body is designed in one piece, and the fluid outlet openings, the at least one fluid-conducting channel and, if appropriate, the fluid reservoir are formed integrally in this hollow profile body.

In a further embodiment of the invention, the hollow profile body is provided with attachment means for a fluid reservoir and/or an actuation mechanism for delivering a liquid additive in the direction of the fluid outlet openings. A syringe or a different form of container can be provided as fluid reservoir. The attachment means provided are preferably Luer connection means in the form of Luer lock or Luer slip connection profiles.

In a further embodiment of the invention, the surgical tissue fusion instrument has a sensor or a sensor arrangement. The sensor or the sensor arrangement can be an electronic sensor or an electronic sensor arrangement, a temperature sensor or a temperature sensor arrangement or an optical sensor, in particular a spectroscopic sensor, or an optical sensor arrangement, in particular a spectroscopic sensor arrangement. The sensor or the sensor arrangement is preferably integrated in a handle of the surgical tissue fusion instrument.

In a further embodiment of the invention, the surgical tissue fusion instrument has an energy source, in particular a current generator, preferably a high-frequency current generator, a radio-frequency generator, an ultrasonic wave generator, a microwave generator or a light source, in particular a laser. The energy source is preferably integrated in a handle of the surgical tissue fusion instrument.

In a further embodiment of the invention, the surgical tissue fusion instrument has an energy-transmitting means that is designed to transmit energy from an energy source of the surgical tissue fusion instrument to at least one of the two gripping structures, in particular to both gripping structures, preferably to the one or more heat-generating means. The transmitting element can, for example, be in the form of electrical lines or light guides, i.e. transparent components such as fibers, tubes or rods, which can transport light over short or long distances.

In a further embodiment of the invention, the surgical tissue fusion instrument has an accumulator. The accumulator is designed to supply current to the tissue fusion instrument, in particular to an energy source integrated therein. The accumulator can in principle be an accumulator cell or an accumulator pack. The accumulator is preferably (likewise) integrated in a handle of the surgical tissue fusion instrument.

Further advantages and features of the invention will become clear from the claims and also from the following description of preferred exemplary embodiments of the invention that are shown in the drawings.

Figure 2:
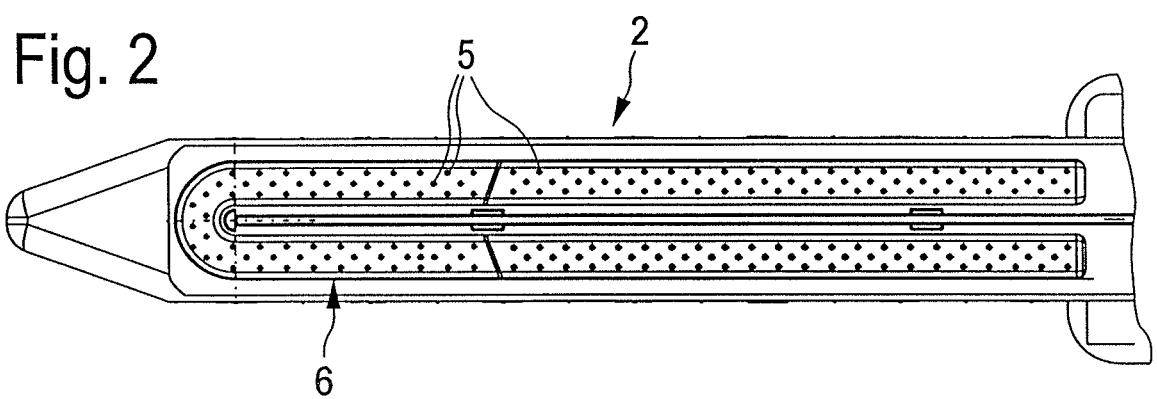
Figure 3:
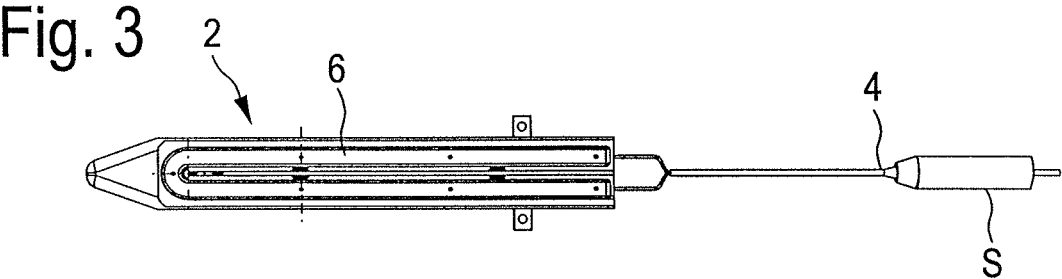
Figure 4:
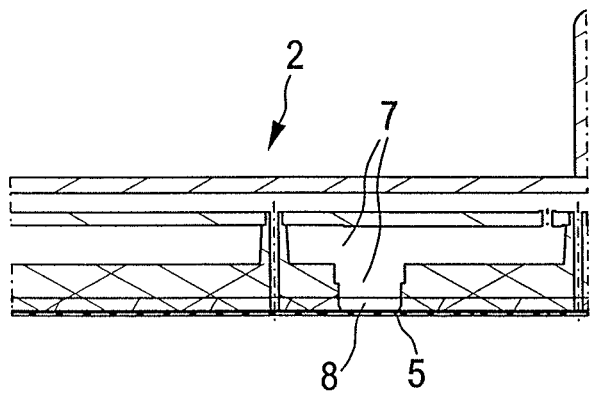
Figure 5:
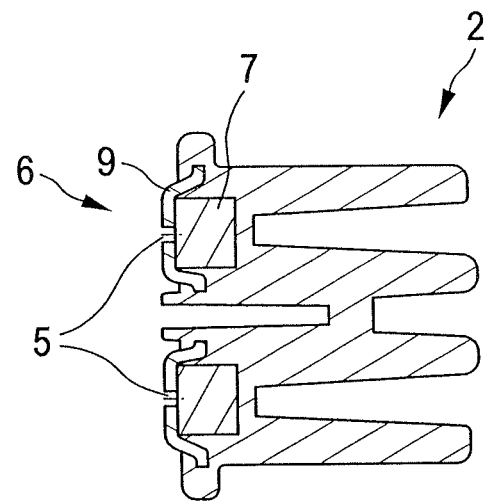
Figure 6:
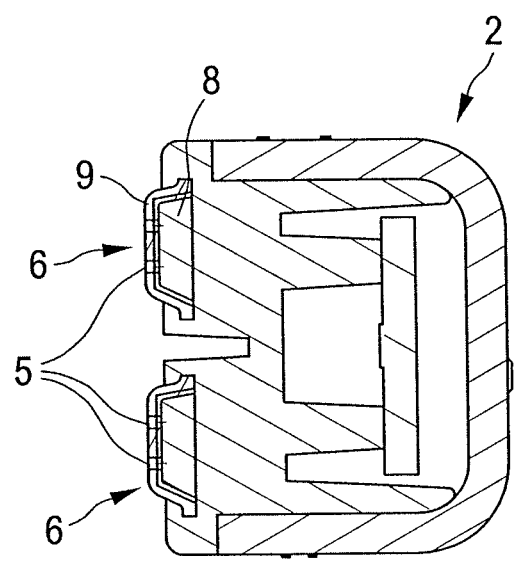
Figure 7:
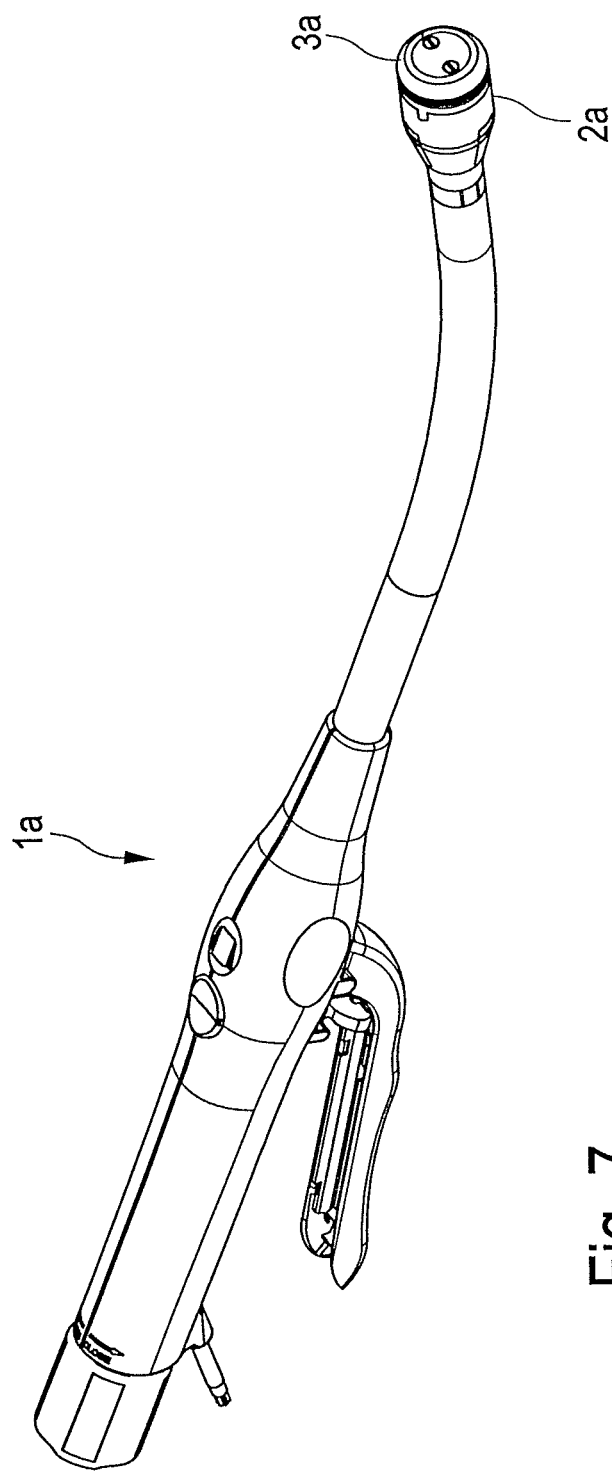
Figure 8:
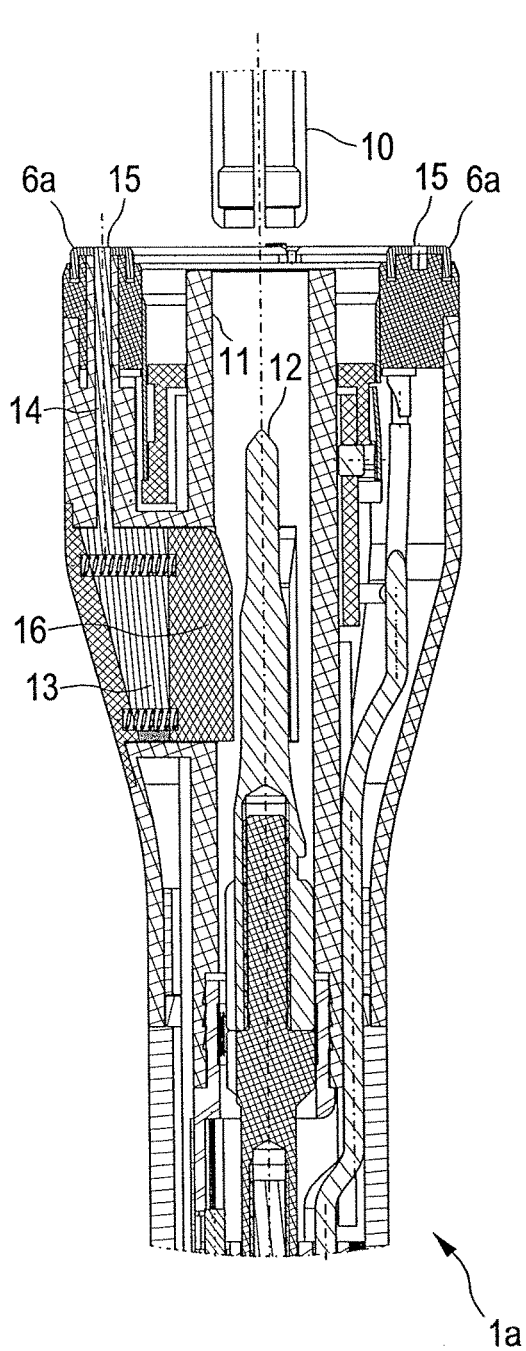
Figure 9:
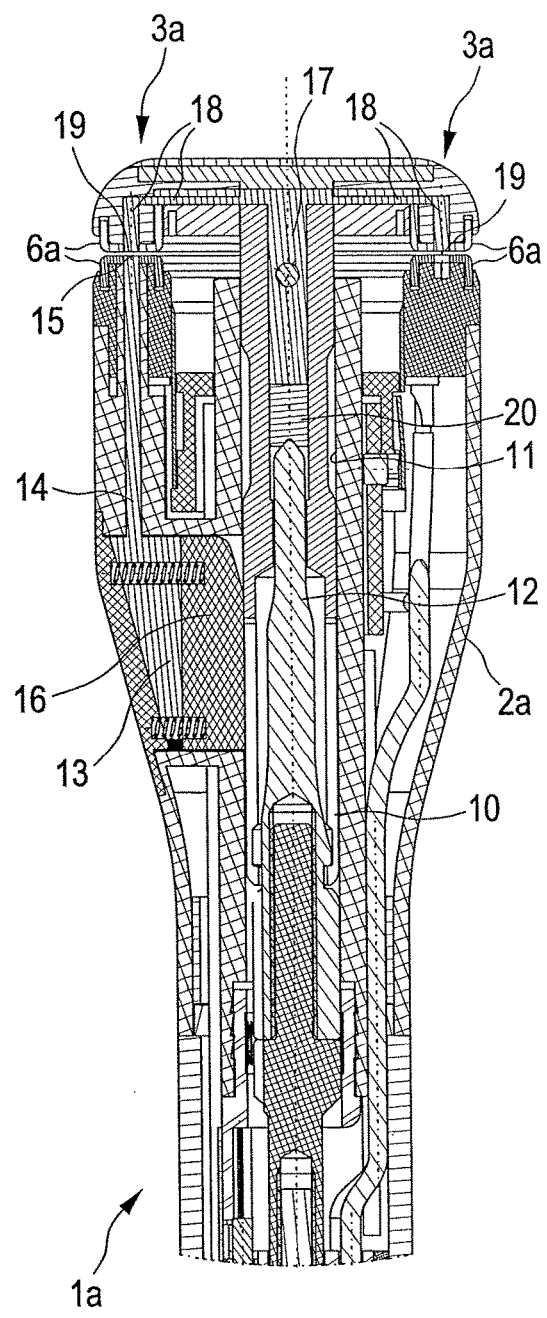

FIG. 1 shows an embodiment of a surgical tissue fusion instrument according to the invention in a linear form, FIG. 2 shows an enlarged view of a gripping structure of the tissue fusion instrument according to FIG. 1, FIG. 3 shows a smaller view of the gripping structure according to FIG. 2 with an attached fluid reservoir, FIG. 4 shows a cross-sectional view of a detail of the gripping structure according to FIG. 2 in the area of a fluid-conducting channel; and of several fluid outlet openings, FIGS. 5 and 6 show further cross-sectional views through the forceps part, from which the arrangements of fluid-conducting channels and fluid outlet openings can be seen, FIG. 7 shows a further embodiment of a surgical tissue fusion instrument according to the invention in a circular form, FIG. 8 shows an enlarged longitudinal section through a partial area of the tissue fusion instrument according to FIG. 7 before base part and anvil part are brought together, FIG. 9 shows the embodiment according to FIG. 8 with anvil part and base part brought together, FIG. 10 shows partial areas of the tissue fusion instrument according to FIGS. 7 to 9 with an anvil part before connection to a trocar mandrel, FIG. 11 shows the view according to FIG. 10, but after the anvil part has been connected to the trocar mandrel, FIG. 12 shows a further embodiment of an anvil part similar to FIGS. 10 and 11 for use in a tissue fusion instrument according to FIGS. 8 and 9, FIG. 13 shows the anvil part according to FIG. 12, with its fluid reservoir in the actuated position, FIG. 14 shows an exploded view of a further embodiment of a tissue fusion instrument according to the invention similar to FIG. 7, FIG. 15 shows the tissue fusion instrument according to FIG. 14 in the assembled state, FIG. 16 shows a cross-sectional view of a partial area of a further embodiment of a tissue fusion instrument according to the invention, similar to FIGS. 7 to 15, with combined fluid-conducting units, FIG. 17 shows a hollow profile body, according to FIGS. 14 and 15, serving as a carrier housing for the fluid-conducting system, and FIG. 18 shows a cross section through the hollow profile body according to FIG. 17 along the section line XVIII-XVIII.

A surgical tissue fusion instrument 1 according to FIGS. 1 to 6 is a linear tissue fusion instrument. The linear tissue fusion instrument 1 according to FIGS. 1 to 6 has two gripping structures 2, 3 which are movable relative to each other, of which a lower gripping structure 3 is held stationary, i.e. in a fixed position, relative to a base part (not shown in detail) of the tissue fusion instrument 1. The upper gripping structure 2 in FIG. 1 is arranged on an upper part that is reciprocatingly movable relative to the base part, such that the two gripping structures 2, 3 can be moved linearly toward or away from each other in the vertical direction. The gripping structures 2, 3 therefore bring about a linear clamping of the corresponding biological tissue sections as soon as the tissue fusion instrument 1 is closed by means of the gripping structures 2, 3 being brought together. Between the gripping structures 2, 3, biological tissue sections are connected to each other along a linear connection site. Each gripping structure 2, 3 has an electrode arrangement 6 as heat-generating means, and electric current can be applied to the electrode arrangement 6 in order to introduce heat into the biological tissue sections in the area of the connection site. The introduction of heat via the electrode arrangements 6 brings about the desired tissue fusion. The electrode arrangements 6 are designed as high-frequency electrodes. The gripping structures 2, 3 can additionally comprise a cutting tool (not shown in detail) so as to be able to separate excess tissue material.

Each electrode arrangement 6 in the gripping structures 2, 3 has an electrode surface, said electrode surfaces extending lengthwise in a flat formation in mutually parallel planes. Each electrode surface is part of a contact surface of each gripping structure 2, 3 which, upon closure of the tissue fusion instrument, will contact the tissue sections and clamp these between them. In the embodiment, according to FIGS. 2 and 3, the electrode surfaces are routed in the manner of a U-shaped loop. Corresponding electrode surfaces of the mutually facing electrode arrangements 6 of the two gripping structures 2, 3 are additionally provided with a multiplicity of fluid outlet openings 5 in order to be able, during a tissue fusion procedure, to apply a liquid or flowable additive directly in the area of the connection site between the biological tissues sections that are to be connected. The fluid outlet openings 5 constitute mouth regions of fluid-conducting channels or fluid reservoirs 7, 8 that are integrated in the respective gripping structure 2, 3.

It is also possible, according to the invention, to provide only one of the two gripping structures 2, 3 with fluid-conducting channels 7, 8 and with fluid outlet openings 5 for the at least one liquid or flowable additive, such that a corresponding additive is supplied only in one gripping structure 2. In this embodiment, during a tissue fusion procedure, the additive is applied to the connection site between the biological tissue sections only from one side.

The fluid-conducting channels 7, 8 additionally form a fluid reservoir for the at least one liquid or flowable additive. Thus, at least parts of the fluid-conducting channels 7, 8 also form a fluid reservoir for the additive in the sense of the invention. The fluid-conducting channels 7, 8 are also designed, by way of attachment means in the form of an attachment nozzle 4, to allow additive to be topped up according to requirements from a syringe S that likewise serves as fluid reservoir. The attachment nozzle 4 is connected to the above-described fluid reservoir via a hose line or tube line, which serves as fluid-conducting channel. Accordingly, a fluid-conducting system, composed of fluid-conducting channels 7, 8, fluid outlet openings 5 and at least one fluid reservoir, is integrated in at least one gripping structure 2.

The different parts of the fluid-conducting channels 7, 8 and, accordingly, the different volumes of the fluid-conducting channels 7,8 can be seen from FIGS. 5 and 6, which show various cross sections along the gripping structure 2. It can also be seen that the electrode surface of the electrode arrangement 6 is formed by a strip-shaped or leaf-shaped electrode wall 9, which is floatingly mounted in a dimensionally stable structural body of the gripping structure 2. In the area of its surface, the structural body forms part of the contact face of the gripping structure 2. The electrode wall 9 is thermally and/or electrically conductive. The fluid outlet openings 5 are introduced into the electrode wall 9.

It can be seen from FIGS. 5 and 6 that the strip-shaped or leaf-shaped electrode walls 9 of the electrode arrangements 6 close off the respective fluid reservoir formed in the gripping structure, i.e. the fluid-conducting channels or fluid reservoir 7 and 8, with respect to the connection site. The electrode walls 9 are mounted in a floating manner or, alternatively, are elastically flexible. As soon as the tissue fusion instrument 1 is closed by means of the gripping elements 2, 3 being brought together, the electrode walls 9 are necessarily displaced or deformed, as a result of which an increased pressure is established in the fluid reservoirs, which increased pressure has the effect that the liquid or flowable additive is pressed, i.e. conveyed, out of the fluid outlet openings 5 in the direction of the connection site.

A surgical tissue fusion instrument 1a according to FIGS. 7 to 11 is, like the above-described tissue fusion instrument 1, intended to connect biological tissue sections to each other, in particular without staples, by bringing them together, clamping them and supplying heat, i.e. to fuse said tissue sections. The surgical tissue fusion instrument 1a according to FIGS. 7 to 11 is designed as a circular tissue fusion instrument, with which biological tissue sections in the form of hollow organs can be connected to each other. In the circular tissue fusion instrument too, thermal energy is supplied to a circular connection site via circularly arranged electrode arrangements 6a, which are designed as high-frequency electrodes. The circular tissue fusion instrument 1a also has two gripping structures 2a, 3a, which are arranged movably relative to each other, in order to be pressed against each other or moved away from each other. One gripping structure 3a is mounted so as to be linearly movable relative to the other gripping structure 2a, as is described in more detail below. The linearly movable gripping structure 3a is also referred to as an anvil part, whereas the opposite gripping structure 2a, which remains stationary relative to the tissue fusion instrument 1a, is referred to as a base part. The tissue fusion instrument 1a is assigned an energy supply line (not shown) which, in particular as a power cable delivering electrical energy via a mains network during the operation of the tissue fusion instrument 1a, introduces the desired heat into the connection site between the gripping structures 2a, 3a by way of the electrode arrangements 6a. Alternatively, the tissue fusion instrument 1a can be supplied with current by means of an accumulator. The use of an accumulator has the particular advantage of permitting the installation of an energy source, in particular a high-frequency current generator, into the surgical tissue fusion instrument 1a. In this case, the energy source and the accumulator are preferably integrated in a handle of the tissue fusion instrument 1a.

The anvil part 3a has an anvil shaft 10, which can be plugged coaxially onto a trocar mandrel 12 mounted longitudinally displaceably in the base part 2a, coaxially with respect to a central longitudinal axis, and which can be locked thereon (FIGS. 8 and 9).

It can be seen from FIGS. 8 and 9 that an annular cutting unit is positioned in the base part 2a, radially inside the electrode arrangement 6a, which cutting unit is part of a cutting device integrated in the tissue fusion instrument 1a. The cutting device can be mechanical and comprise at least one cutting blade, or it can be non-mechanical, in particular in the form of a laser cutter. The annular cutting blade (not shown in detail) can be moved if necessary into a connection plane between the anvil part 3a and the base part 2a, in order to effect a circular separation of the interconnected tissue sections.

The base part 2a of the tissue fusion instrument 1a is assigned a fluid reservoir 13, which is integrated in a receiving portion of the base part 2a. The fluid reservoir 13 is provided for the storage of a liquid or flowable additive and is connected by way of one or more fluid-conducting channels 14 to fluid outlet openings 15 in the area of the annular electrode arrangement 6a. The fluid outlet openings 15 are integrated in corresponding electrode surfaces of the electrode arrangement 6a. The electrode surfaces are formed by at least one strip-shaped or leaf-shaped electrode strip, which is held in an end face of the base part 2a (FIGS. 8 and 9). The electrode strip is also referred to as the electrode wall. Analogously to the design of the linear tissue fusion instrument, contact faces of the gripping structures 2a, 3a are formed by electrode arrangements and adjacent surfaces of the structural bodies of the gripping structures 2a, 3a supporting the electrode arrangements.

The fluid reservoir 13 in the base part 2a can be acted on by an actuation mechanism, by which means a volume of the fluid reservoir 13 is compressible. The corresponding pressure build-up inevitably leads to a discharge of the additive through the fluid outlet openings 15. The fluid reservoir 13 has an actuation button 16 which protrudes radially inward into a guide channel 11 of the base part 2a and which is supported on an outer wall of the fluid reservoir 13 via a spring arrangement in the form of helical compression springs. The actuation button 16 is mounted so as to be linearly movable radially with respect to the guide channel 11. In the present case, the anvil shaft 10 has an outer jacket with axially extending recesses which interact with the actuation button 16 in such a way that an outer jacket of the anvil shaft 10 above the axial recesses comes into contact with the actuation button 16 as soon as the anvil part 3a has moved to its closed position. In this way, the actuation button 16 is pressed radially outward and leads to the pressure build-up inside the fluid reservoir 13, which brings about the desired application of additive in the area of the fluid outlet openings 15 of the base part 2a.

A fluid-conducting system for discharging a liquid or flowable additive is also integrated in the anvil part 3a. The fluid-conducting system in the anvil part 3a comprises a fluid reservoir 17, fluid-conducting channels 18 and fluid outlet openings 19. The fluid reservoir 17 is formed in the anvil shaft 10. For this purpose, the anvil shaft is hollow. On a side facing the trocar mandrel 12, the fluid reservoir 17 is closed by means of a closure piston 20 serving as actuation wall. As soon as the anvil part 3a is guided to the closed position of the tissue fusion instrument, as a result of which an anvil head of the anvil part 3a is pressed against an end face of the electrode arrangement 6a of the base part 2a, the anvil shaft 10 moves relative to the trocar mandrel 12. This inevitably causes a movement of the closure piston 20 along the anvil shaft 10 in the direction of the anvil head, as a result of which the volume of the fluid reservoir 17 is compressed. This necessarily leads to a fluid discharge of the additive in the area of the fluid outlet openings 19.

Upon closure of the circular tissue fusion instrument 1a, the liquid or flowable additive is therefore supplied at the same time from opposite sides in the area of the connection site, both from the base part 2a and also from the anvil part 3a.

Alternatively to the anvil part 3a according to FIGS. 10 and 11, it is also possible for the circular tissue fusion instrument 1a according to FIGS. 7 to 9 to be operated with an anvil part 3b according to FIGS. 12 and 13. This anvil part 3b differs from the anvil part 3a in that the anvil shaft 10b is arranged to be coaxially movable relative to the anvil head. For this purpose, a head plate 22 is arranged on the end face of the anvil shaft 10b and forms an upper actuation wall for a fluid reservoir 17b arranged in the anvil head. A movement of the anvil shaft 10b relative to the anvil head causes a reduction in volume of the fluid reservoir 17b, such that additive is applied through fluid-conducting channels 18b in the area of the fluid outlet openings 19b. In order to achieve a corresponding pressure build-up, the anvil part 3b is moved to its closed position relative to the base part. As soon as the anvil head in the area of the connection site comes to bear on the end face of the base part, the anvil head is blocked against further longitudinal movement. By contrast, the trocar mandrel (not shown) moves the anvil shaft 10b onward in the same direction, as a result of which the anvil shaft 10b, by way of a connecting pin 21 providing a form-fit connection, entrains the cover plate 22 serving as piston, such that a desired reduction in volume takes place in the fluid reservoir 17b.

In the embodiment according to FIGS. 14 and 15 and also FIGS. 17 and 18, the circular tissue fusion instrument 1c is likewise assigned a fluid-conducting system in order to supply a liquid or flowable additive in the area of the connection site between anvil part 3c and base part 2b according to requirements. In this embodiment, however, the delivery of the additive does not take place axially as in the above-described embodiments, but instead radially from the outside. For this purpose, a carrier housing 23 in the form of a hollow-body profile is provided, which is slit continuously along its length by means of an expansion slit 27. The hollow-body profile is sleeve-shaped or tubular and is designed with a double wall in order to form, in the double-wall area, a plurality of fluid-conducting channels 25 distributed about the circumference of the hollow-body profile. The fluid-conducting channels are distributed annularly about the hollow-body profile and extend along the entire length of the hollow-body profile between radially inwardly directed fluid outlet openings 24 in the area of an end face of the hollow-body profile and an inlet nozzle 26, serving as attachment means, on an opposite end area of the hollow-body profile. The inlet nozzle 26 serves to attach a fluid reservoir in which the additive is stored. Alternatively, the additive can also be stored directly in the fluid-conducting channels 25. In this embodiment, the inlet nozzle serves as an attachment means for an actuation mechanism in order to be able to build up pressure in the fluid-conducting channels 25 and, accordingly, permit a discharge of the additive in the area of the fluid-outlet openings 24.

FIG. 16 shows a further circular tissue fusion instrument 1d similar to the above-described embodiments. An important difference as regards the tissue fusion instrument 1d is that, in the latter, all of the fluid-conducting systems present in the above-described embodiments according to FIGS. 7 to 15, 17 and 18 are all combined with one another. This means that the base part 2c is, on the one hand, enclosed by a carrier housing 23 according to FIGS. 14 and 15, 17 and 18. On the other hand, the fluid-conducting systems are provided in the base part 2c and in the anvil part 3c, as has already been described above with reference to FIGS. 8 to 11.

The invention claimed is:

1. A surgical tissue fusion instrument with two gripping structures which are movable relative to each other, are designed for gripping and bringing together biological tissue sections, and are assigned heat-generating means designed in such a way that tissue fusion takes place between the biological tissue sections by heat being supplied in the area of the gripping structures, wherein at least one gripping structure is assigned a fluid-conducting system, which is designed to supply at least one liquid or flowable additive to the tissue sections during a tissue fusion procedure, wherein the fluid-conducting system has at least one fluid-conducting channel, which is integrated in one of the two gripping structures, at least one gripping structure is provided with fluid outlet openings, into which the at least one fluid-conducting channel opens, the fluid-conducting channel has a reservoir volume that is variable depending on an actuation mechanism, wherein the actuation mechanism is operatively connected to an actuation unit for bringing together the gripping structures, wherein the fluid outlet openings are integrated into at least one electrode arrangement, which is assigned to the heat generating means, and wherein the fluid outlet openings are provided in a movably mounted actuation wall of the at least one fluid-conducting channel, which actuation wall, depending on an activation of the actuation unit, is movable in order to bring together the gripping structures, wherein the actuation wall is formed by an electrode wall of the at least one electrode arrangement.

2. The surgical tissue fusion instrument of claim 1, wherein the fluid-conducting system has at least one fluid reservoir, which is connected to the fluid-conducting channel.

3. The surgical tissue fusion instrument of claim 2, wherein the at least one fluid reservoir is integrated in at least one gripping structure.

4. The surgical tissue fusion instrument of claim 2, wherein the at least one fluid reservoir has a reservoir volume that is variable depending on an actuation mechanism.

5. The surgical tissue fusion instrument of claim 2, wherein the fluid conducting system is integrated in a carrier housing which encloses at least a partial area of the tissue fusion instrument and which is provided with the at least one fluid reservoir and also with the fluid outlet openings.

6. The surgical tissue fusion instrument of claim 2, wherein the at least one fluid reservoir is positioned separate from the tissue fusion instrument, and wherein attachment means are provided for producing or cancelling a connection between the at least one fluid reservoir and the at least one fluid-conducting channel of the tissue fusion instrument.

7. The surgical tissue fusion instrument of claim 1, wherein the actuation mechanism is positioned separate from the tissue fusion instrument, and attachment means are provided for producing or canceling a connection between the actuation mechanism and the at least one fluid-conducting channel of the tissue fusion instrument.

8. The surgical tissue fusion instrument of claim 1, wherein the fluid-conducting system is integrated in a carrier housing which encloses at least a partial area of the tissue fusion instrument and which is provided with the at least one fluid-conducting channel and also with the fluid outlet openings.

9. The surgical tissue fusion instrument of claim 8, wherein the fluid outlet openings in the carrier housing are positioned in the area of a dividing plane between the gripping structures, and in that the fluid outlet openings are directed radially from the outside toward the dividing plane.

10. The surgical tissue fusion instrument of claim 8, wherein a circular tissue fusion instrument is provided, and the carrier housing is designed as a hollow profile body which forms a sleeve-shaped or tubular enclosure around a base part of the circular tissue fusion instrument and which is provided with an expansion slit extending along its entire length, so as to be able to mount the hollow profile body on the base part or detach it therefrom.

11. The surgical tissue fusion instrument of claim 10, wherein the hollow profile body is provided with attachment means for a fluid reservoir and/or an actuation mechanism for conveying a liquid or flowable additive in the direction of the fluid outlet openings.

12. The surgical tissue fusion instrument of claim 1, wherein the electrode wall is mounted in a floating manner.

13. The surgical tissue fusion instrument of claim 1, wherein the electrode wall is elastically flexible.

* * * * *